(12) United States Patent
Oda et al.

(10) Patent No.: US 8,945,072 B2
(45) Date of Patent: Feb. 3, 2015

(54) HEAT GENERATING DEVICE

(75) Inventors: Hideshi Oda, Tokyo (JP); Hidetoshi Taima, Tokyo (JP); Shuji Ishikawa, Tokyo (JP); Yasuto Saita, Tokyo (JP)

(73) Assignee: Kao Corporation, Tokyo (JP)

( * ) Notice: Subject to any disclaimer, the term of this patent is extended or adjusted under 35 U.S.C. 154(b) by 278 days.

(21) Appl. No.: 13/122,616

(22) PCT Filed: Dec. 4, 2009

(86) PCT No.: PCT/JP2009/070409
§ 371 (c)(1),
(2), (4) Date: Apr. 5, 2011

(87) PCT Pub. No.: WO2010/067761
PCT Pub. Date: Jun. 17, 2010

(65) Prior Publication Data
US 2011/0190714 A1 Aug. 4, 2011

(30) Foreign Application Priority Data

Dec. 10, 2008 (JP) ................................. 2008-314424
Jun. 19, 2009 (JP) ................................. 2009-146987
Oct. 2, 2009 (JP) ................................. 2009-230938
Oct. 2, 2009 (JP) ................................. 2009-230957

(51) Int. Cl.
*A61M 35/00* (2006.01)
*C09K 5/16* (2006.01)
*A61F 7/03* (2006.01)

(52) U.S. Cl.
CPC ... *C09K 5/16* (2013.01); *A61F 7/03* (2013.01); *A61F 7/034* (2013.01)
USPC ........................................ 604/291; 424/449

(58) Field of Classification Search
CPC ............... A61B 18/14; A61B 18/1492; A61B 2018/046; A61F 7/00; A61F 7/007; A61F 7/0085; A61F 7/02; A61F 7/03; A61F 7/034; A61F 7/12; A61F 7/123; A61F 2007/0001; A61F 2007/0242; A61F 2007/026; A61F 2007/126; A61K 8/02; A61K 9/70; A61K 19/00; A61L 15/28; A61L 15/44; A61L 15/46; A61L 2300/404; A61M 1/00; A61M 1/008; A61M 1/0088; A61M 5/44; A61M 2205/3653
USPC .................. 604/113, 291, 304; 429/443, 449; 607/96, 114
See application file for complete search history.

(56) References Cited

U.S. PATENT DOCUMENTS 6,546,281 B1 * 4/2003 Zhang et al. .................... 604/20
2007/0020412 A1 * 1/2007 Kumamoto et al. ......... 428/34.2
2007/0110790 A1 5/2007 Igaki et al.

FOREIGN PATENT DOCUMENTS

JP 2001 187727 7/2001
JP 2001-187727 7/2001

(Continued)

OTHER PUBLICATIONS

International Search Report issued Dec. 28, 2009 in PCT/JP09/70409 filed Dec. 4, 2009.

(Continued)

*Primary Examiner* — Melanie Hand
(74) *Attorney, Agent, or Firm* — Oblon, Spivak, McClelland, Maier & Neustadt, L.L.P.

(57) ABSTRACT

A heat generating device includes a holder and a heat generating member that is enclosed in the holder and that contains an oxidizable metal, a reaction accelerator, an electrolyte, and water. The heat generating member contains a transdermally-absorbable medicament and a solvent for dissolving the transdermally-absorbable medicament. It is preferable that the solvent is at least one type of polyol selected from polyols that are in their liquid state at 25° C. It is also preferable that the heat generating member further contains at least one type of solvent composed of an oily agent that is in its liquid state at 25° C. It is also preferable that the heat generating member further contains a surfactant. It is also preferable that the polyol is polyethylene glycol.

9 Claims, 4 Drawing Sheets

(56) References Cited

FOREIGN PATENT DOCUMENTS

| | | |
|---|---|---|
| JP | 2001 224621 | 8/2001 |
| JP | 2003 116902 | 4/2003 |
| JP | 2003 210509 | 7/2003 |
| JP | 2003 327527 | 11/2003 |
| JP | 2007 236725 | 9/2007 |

OTHER PUBLICATIONS

Combined Chinese Office Action and Search Report issued Jan. 21, 2013 in Chinese Patent Application No. 200980148178.8 (with English-language translation).

* cited by examiner

HEAT GENERATING DEVICE

CROSS REFERENCES TO RELATED APPLICATIONS

This application is a 371 of International Patent Application No. PCT/JP2009/070409, filed on Dec. 4, 2009, and claims priority to Japanese Patent Application No. 2008-314424, filed on Dec. 10, 2008, Japanese Patent Application No. 2009-146987, filed on Jun. 19, 2009, Japanese Patent Application No. 2009-230938, filed on Oct. 2, 2009, and Japanese Patent Application No. 2009-230957, filed on Oct. 2, 2009.

TECHNICAL FIELD

The present invention relates to a heat generating device that is used on the human body to provide a warm feeling thereto.

BACKGROUND ART

Applicant has proposed a steam-generating warming sheet having a heat generating sheet and a holder for enclosing the heat generating sheet therein (see Patent Literature 1 below). The heat generating sheet contains an oxidizable metal and an aqueous electrolytic solution, and can generate heat upon contact with air. The holder is air-permeable at least partially. The steam-generating warming sheet releases warm steam outside through the holder. When worn on the human body, the steam-generating warming sheet not only raises the surface temperature in the area of use, but also raises the temperature deep inside the body, thereby increasing the amount of blood flow throughout the body. This is advantageous in that, not only the temperature in the area of use, but also the peripheral temperature such as the temperature at the fingertips can be raised. However, since this steam-generating warming sheet raises the skin temperature in the area of the body where it is worn to around 40° C. and thus makes the user feel hot, the user may tend to refrain from using this steam-generating warming sheet in the summertime.

Besides the above steam-generating warming sheet, Applicant has also proposed a steam generating element having a steam generating composition composed of metal power, salts, and water and designed to release steam upon oxidation of the metal power (see Patent Literature 2 below). The steam generating composition dispersedly contains cosmetic components or medicinal components, and accordingly, the steam generating element can continuously supply the cosmetic components or medicinal components along with the heated steam. Essential oils, aroma components such as menthol, and herbal extracts, for example, can be used as the cosmetic components or medicinal components. In cases where these components are insoluble in water, they are dispersed in water with a dispersing agent such as a surfactant and added to the steam generating composition as an emulsion.

CITATION LIST

Patent Literature

Patent Literature 1: US 2007/0110790A1
Patent Literature 2: JP 2001-187727A

SUMMARY OF INVENTION

Simply dispersing the above components with a dispersing agent such as a surfactant, however, may require some time for the components to take effect. Further, in some cases, the components' effects may not be sufficient.

The present invention provides a heat generating device including a holder and a heat generating member that is enclosed in the holder and that contains an oxidizable metal, a reaction accelerator, an electrolyte, and water. The heat generating member contains a transdermally-absorbable medicament and a solvent for dissolving the transdermally-absorbable medicament.

The present invention also provides a preferable method of manufacturing the heat generating device, including: preparing a heat generating member by adding, to a mixture containing an oxidizable metal, a reaction accelerator, an electrolyte, and water, a solution obtained by dissolving a transdermally-absorbable medicament into a solvent.

Advantageous Effects of Invention

According to the present invention, the heat generated by the heat generating member remarkably improves the releasing properties of the transdermally-absorbable medicament to the skin and thus allows the medicament's physiological effects to be exerted on the user effectively. Furthermore, the temperature at which the heat is generated can be made uniform across the entire heat generating member and can also be kept constant.

Particularly in cases where the transdermally-absorbable medicament is a cool-feeling agent that provides a cool feeling to the skin, it is possible to provide heat to the user without actually lowering the skin temperature, even though the user has a cool-and-refreshing feel.

DESCRIPTION OF EMBODIMENTS

Figure 1:
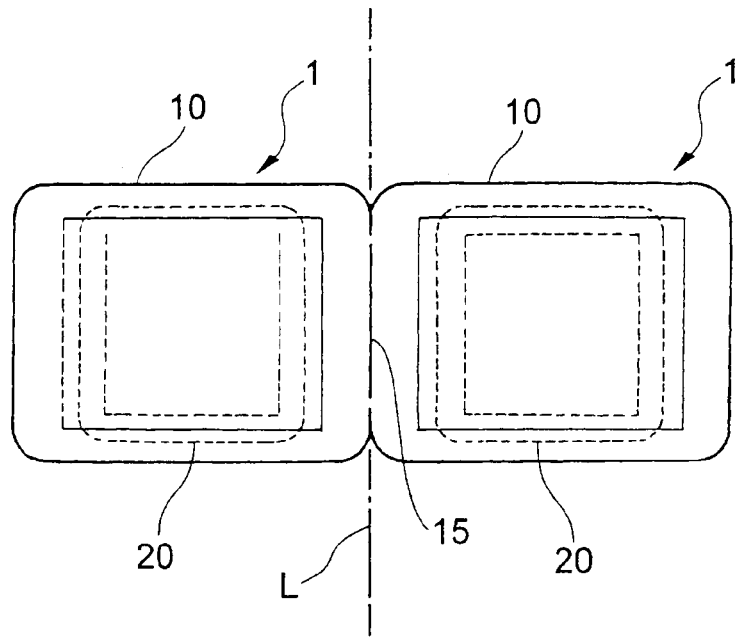
FIG. 1 is a plan view illustrating a heat-and-steam generating device as an embodiment of a heat generating device of the present invention.
Figure 2A:
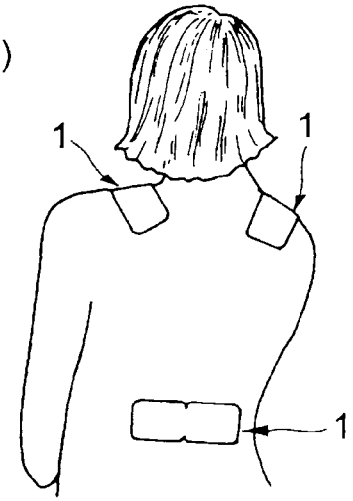
FIG. 2(*a*) and FIG. 2(*b*) are explanatory diagrams illustrating how the heat-and-steam generating device of FIG. 1 is used.
Figure 2B:
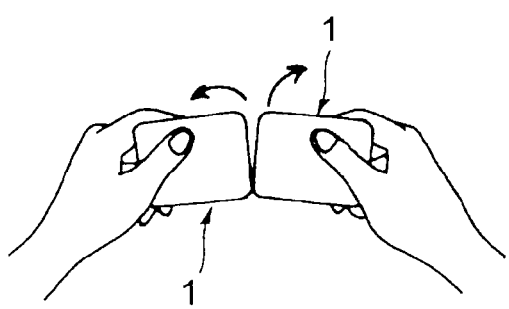

The present invention will be described below according to preferred embodiments thereof with reference to the drawings. The present invention relates to a heat generating device that allows the effectiveness of medicinal components to be exerted far more effectively compared to conventional devices described above. FIG. 1 is a plan view of a heat-and-steam generating device serving as an embodiment of the heat generating device of the invention. The heat-and-steam generating device 1 of the present embodiment is basically composed of a bag 10 and a heat generating element 20. FIG. 1 illustrates two heat-and-steam generating devices connected together. The heat generating element 20 is enclosed in the bag 10. The heat-and-steam generating device 1 of the present embodiment is used by being attached directly to the body of a wearer, either in a connected state where two of the devices are connected as illustrated in FIG. 2(*a*) or in a separate state where the two devices are cut apart as illustrated in FIG. 2(*b*). The heat-and-steam generating device 1 includes a heat generating member, and is designed to continuously supply, to the area of the wearer's body where the device is attached, a transdermally-absorbable medicament and steam generated by the heat generating member and heated to a prescribed elevated temperature.

As regards the heat-and-steam generating device 1 of the present embodiment, two heat-and-steam generating devices 1 are connected together, and no heat generating element 20 exists in the area where the devices are connected. Therefore, the pair of heat-and-steam generating devices 1 can easily fold in half, utilizing the area of connection as a folding line. That is, the pair of heat-and-steam generating devices 1 can easily bend both inward and outward at the area of connection. Accordingly, the heat-and-steam generating devices 1 can be attached to either the inner or the outer side of a joint of the elbow, the knee, etc. To take more advantage of this effect, it is preferable to form linearly-arranged slits (cuts) 15 (see FIG. 1) or perforations (not shown) along a vertical centerline L between the bags 10. The slits 15 or perforations allow the two heat generating elements 20 to separate from each other easily, thereby helping the pair of heat-and-steam generating devices 1 to smoothly comfort to the bending of the joint. The heat-and-steam generating device 1 of the present embodiment has an advantage of being favorably conformable particularly to twisting movement. The linearly-arranged slits 15 may be formed as a single continuous row of short slits or as a plurality of continuous rows of slits. Instead, the slits may be replaced with at least one elongated hole having the shape of a rhombus, a rectangle, or an ellipse, for example.

Figure 3:
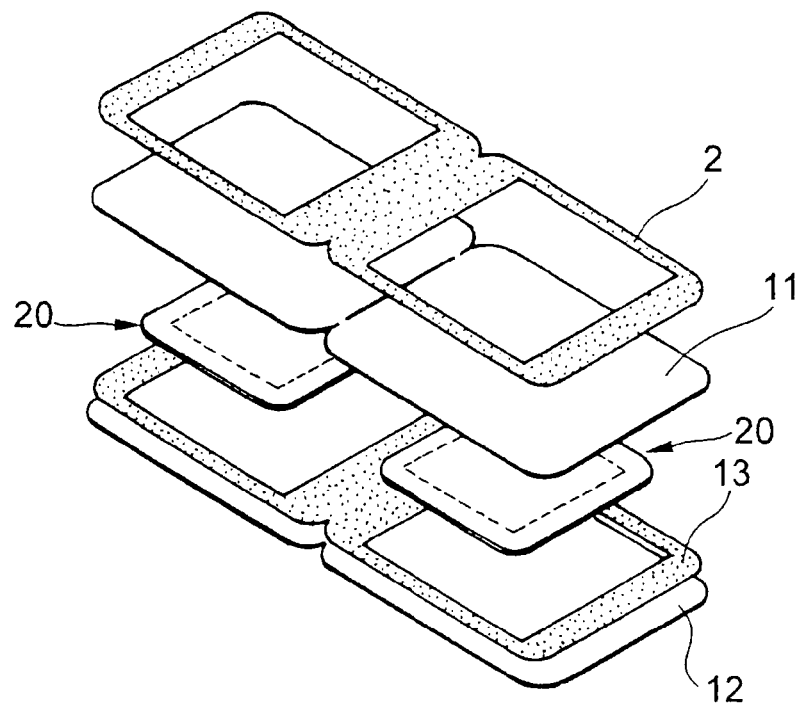
FIG. 3 is an exploded perspective of the heat-and-steam generating device of FIG. 1.

FIG. 3 illustrates an exploded perspective of the heat-and-steam generating device of FIG. 1. The bag 10 includes a first sheet 11 adapted to be located proximal to the wearer's skin and a second sheet 12 adapted to be located distal to the wearer's skin. The two sheets 11, 12 have the same shape and are both substantially rectangular having long sides and short sides. Placing the two sheets 11, 12 one upon the other and joining their perimeters together through joining means 13 will form a bag 10 providing a space inside. Examples of joining means 13 that can be used include heat sealing, ultrasonic sealing, and various bonding agents such as a hot-melt adhesive. There is no particular limitation to the type of material to be used for the sheets 11, 12 as long as they are air-permeable and preferably stretchable. Particularly, it is preferable that the first sheet 11 is made of a material having good texture because it directly comes into contact with the wearer's body. Specific examples may include fibrous sheets made, for example, of: synthetic fibers including polyesters such as PET (polyethylene terephthalate), polyolefins such as PE (polyethylene) and PP (polypropylene), polyamide, and polyacrylate; natural fibers such as cellulose, silk, cotton, and wool; or conjugate fibers of the above. Air-through or spunbonded nonwoven fabrics containing elastic fibers are particularly preferable.

It is preferable that each of the first and second sheets 11, 12 has stretchability in at least one direction. In cases where each sheet 11, 12 is stretchable in only one direction, it is preferable that the stretchable direction coincides with the long-side direction of the substantially rectangular bag 10. In cases where each sheet 11, 12 is stretchable in two directions orthogonal to one another, it is preferable that the stretchable directions respectively coincide with the long-side direction of the substantially rectangular bag 10 and the short-side direction thereof orthogonal thereto. Herein, the term "stretch sheet" is intended to include a sheet having at least one of extensibility and retractability from extension (contractibility). For example, it will suffice if at least one of the sheets 11, 12 is extensible in one direction, but it is preferable that one of the sheets 11, 12 has extensibility while the other has both extensibility and retractability. In another preferred embodiment, both sheets 11, 12 are stretchable in two directions orthogonal to one another, and are both extensible and retractable. The dotted region in FIG. 3 indicated by the numerical symbol "13" illustrates the area in which the two sheets 11, 12 are joined together.

The heat generating element 20 is used to apply steam generated from a heat generating member 21, which is contained in the heat generating element 20, at a prescribed elevated temperature to the wearer's body through the bag 10. The heat generating element 20 is substantially square, and is enclosed in the above-described space inside the bag 10. At this time, the heat generating element 20 is enclosed inside the bag 10 in such a manner that the sides of the heat generating element 20 coincide with the directions of the long sides and short sides of the bag 10.

As illustrated in FIG. 1, the bag 10 is larger than the heat generating element 20 in dimension. The two sheets 11, 12 that form the bag 10 extend outward from the perimeter of the heat generating element 20. In the present embodiment, a substantially-square heat generating element 20 is enclosed inside a substantially-rectangular bag 10. However, the bag 10 and the heat generating element 20 are not limited to these shapes and may be shaped similarly. Further, the bag 10 and the heat generating element 20 may come in various shapes, such as circular, elliptical, rectangular, substantially rhombic, or a broad-bean shape.

As illustrated in FIG. 3, the first sheet 11 of the bag 10 of the heat-and-steam generating device 1 has, on its surface, attachment means 2 for attaching the heat-and-steam generating device 1 to the user's body. The attachment means 2 is provided within a prescribed range on all four sides of the first sheet 11 along the entire perimeter thereof. Examples of the attachment means 2 that can be used include bonding agents such as a hot-melt adhesive.

Figure 4:
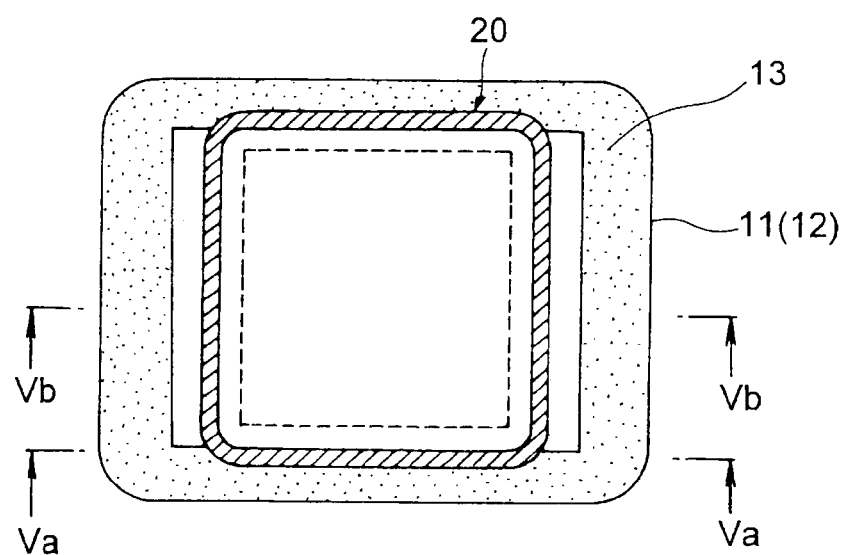
FIG. 4 is a plan view illustrating a positional relationship between a heat generating element and an area in which two sheets have been joined by joining means.
Figure 5A:
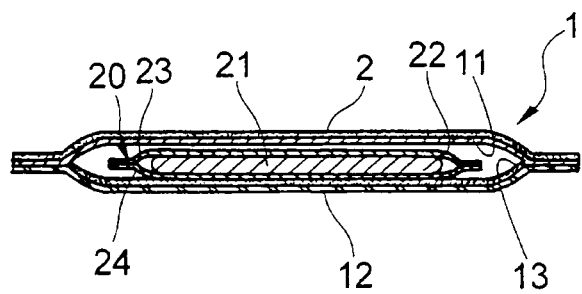
FIG. 5(*a*) is a cross-sectional view taken along line Va-Va in FIG. 4, and FIG. 5(*b*) is a cross-sectional view taken along line Vb-Vb in FIG. 4.
Figure 5B:
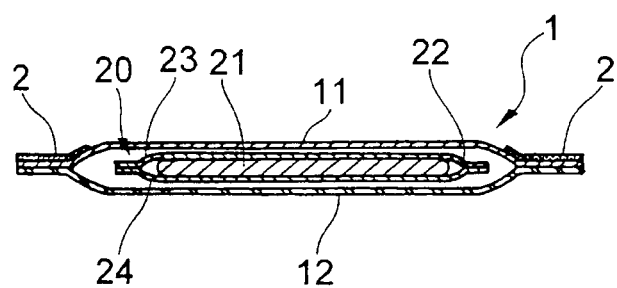

FIG. 4, FIG. 5(*a*), and FIG. 5(*b*) illustrate the positional relationship between the heat generating element 20 and the area in which the two sheets 11, 12 have been joined by the joining means 13. As illustrated in FIG. 4, the joining means 13 is provided within a prescribed range on all four sides of the two sheets 11, 12 along the entire perimeters thereof. On the other hand, the heat generating element 20 is arranged in such a manner that only its upper-side portion and its lower-side portion are placed on the joining means 13, as illustrated in FIG. 4 and FIG. 5(*a*). Thus, the heat generating element 20 is joined to the joining means 13 only at its upper-side portion and its lower-side portion, and as illustrated in FIG. 5(*b*), the rest of the portions of the heat generating element 20 are not joined to the two sheets 11, 12.

In cases where the bag 10 is stretchable, the heat generating element 20 is fixed to the inner side of the bag 10 in such a manner that the stretchability of the bag 10 is not impaired. More specifically, the heat generating element 20 is fixed to the bag 10 at its upper-side portion and its lower-side portion, as illustrated in FIG. 4. This prevents the heat generating element 20 from moving out of place inside the bag 10 while the heat-and-steam generating device 1 is being carried about or while the heat-and-steam generating device 1 is attached to the wearer's body. Accordingly, the heat generating element 20 will stay in the area to be steamed. The position for fixing the heat generating element 20 to the bag 10 is not particularly limited to that illustrated in FIG. 4, as long as the stretchability of the bag 10 is not impaired. Nevertheless, it is preferable that the heat generating element 20 be fixed in such a manner that the bag 10 remains stretchable in the overlap between it and the heat generating element 20 when viewing the heat-and-steam generating device 1 from above, in order to provide the bag 10 with a large stretchable portion.

Figure 6:
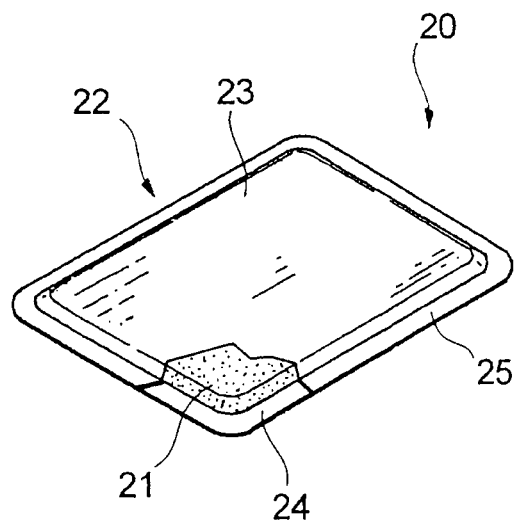
FIG. 6 is a partially-cutaway perspective illustrating a heat generating element in the heat-and-steam generating device of FIG. 1.

FIG. 6 is a perspective illustrating the heat generating element 20 enclosed inside the bag 10, with a portion of the element 20 cut away. The heat generating element 20 includes a heat generating member 21 and a holder 22 holding the heat generating member 21. The holder 22 is flat-shaped and defines the contour of the heat generating member 20. The holder 22 is composed of a plurality of sheet materials joined together to provide a bag-like space in which the heat generating member 21 is held. The flat holder 22 has a first side 23 located proximal to the wearer's skin and an opposite, second side 24 located distal to the user's skin.

The heat generating member 21 is a part that generates steam of a prescribed elevated temperature by making use of the heat accompanying the oxidation reaction between an oxidizable metal and oxygen and that also releases a transdermally-absorbable medicament. The heat generating member 21 contains an oxidizable metal, a reaction accelerator, an electrolyte, and water. The heat generating member 21 of the present embodiment also contains a transdermally-absorbable medicament and a solvent for the medicament. In addition to these components, the heat generating member 21 preferably contains a surfactant. The following describes these agents, the structure and manufacturing method of the heat-and-steam generating device etc., and other embodiments thereof.

Oxidizable Metal

Any oxidizable metal can be used without particular limitation as long as it generates heat through oxidation. Examples include powders or fibers of iron, aluminum, zinc, manganese, magnesium, calcium, or the like. Among these, iron powder is preferably used from the standpoint of handleability, safety, and manufacturing costs. In cases where the oxidizable metal is powdery, it is preferable that the particle diameter is 0.1 to 300 µm. Particularly, it is preferable to use a material that contains at least 50% by mass of particles having particle diameters of 0.1 to 150 µm with respect to the total mass of the oxidizable metal. Containing the oxidizable metal at a percentage of preferably 20 to 80% by mass, more preferably 30 to 70% by mass, and even more preferably 45 to 65% by mass, with respect to the entire mass of the heat generating member 21 would be suitable for securing a sufficient amount of heat generation.

Reaction Accelerator

A reaction accelerator functions as an agent for retaining oxygen and supplying oxygen to the oxidizable metal. It is particularly preferable to use a reaction accelerator that can act as a moisture-retaining agent. Examples include activated carbon (such as coconut shell charcoal, charcoal powder, bituminous coal, peat coal, and lignite), carbon black, acetylene black, graphite, zeolite, pearlite, vermiculite, and silica. Among these, activated carbon is preferable because of its moisture retainability, oxygen-supplying ability, and catalytic properties.

The particle diameter of the reaction accelerator is preferably 0.1 to 500 µm from the standpoint of providing effective contact with the oxidizable metal. Particularly, it is preferable to use a material that contains at least 50% by mass of particles having particle diameters of 0.1 to 200 µm with respect to the total mass of the reaction accelerator. Containing the reaction accelerator at a percentage of preferably 0.1 to 20% by mass, more preferably 1 to 15% by mass, and even more preferably 3 to 10% by mass, with respect to the entire mass of the heat generating member 21 would be suitable for sufficiently exerting its reaction-accelerating effect.

Water

Water is preferably contained at a percentage of 10 to 50% by mass, more preferably 15 to 40% by mass, and even more preferably 20 to 35% by mass, with respect to the entire mass of the heat generating member 21, because not only is oxidation reaction of the oxidizable metal favorably accelerated, but also a sufficient amount of steam is generated.

Electrolyte

An electrolyte is a substance that forms an electrolytic solution when dissolved in water. It is particularly preferable that the electrolyte further accelerates oxidation reaction of the oxidizable metal. Examples of electrolytes include sodium chloride, potassium chloride, calcium chloride, and magnesium chloride. Among these, sodium chloride is particularly preferably used from the standpoint of handleability, safety, and manufacturing costs. The electrolyte is contained at a percentage of preferably 0.1 to 15% by mass, more preferably 0.5 to 14% by mass, and even more preferably 1 to 12% by mass, with respect to the entire mass of the heat generating member 21. Containing the electrolyte at this percentage allows the temperature at which the heat is generated to be maintained favorably, and can also prevent inhibition of the functions of the surfactant, which is used as necessary, of emulsifying and dispersing the transdermally-absorbable medicament in the heat generating composition, even in presence of the electrolyte.

Transdermally-Absorbable Medicament

A transdermally-absorbable medicament is a generally-used endermic medicament for cosmetic and medicinal purposes that is released by the generation of heat of the heat generating device and achieves topical and systemic physiologically-activate effects by being absorbed through the skin. Specific examples include: aroma chemicals such as camphor, limonene, geraniol, cedrol, and citronellol; essential oils such as mint oil, peppermint oil, lavender oil, eucalyptus oil, and ginger oil; cool-feeling agents such as menthol, e.g. 1-menthol and dl-menthol, and menthol derivatives (e.g. menthyl lactate); warm-feeling agents such as capsicum tincture, nonylic acid vanillylamide, and capsaicin; blood circulation promoting agents such as tocopherol acetate, tocopherol nicotinate, and benzyl nicotinate; skin whitening agents such as arbutin, Kojic acid, L-ascorbic acid, and L-ascorbic acid derivatives; anti-wrinkle agents such as retinol; local anesthetics such as lidocaine and tetracaine; nonsteroidal anti-inflammatory agents such as methyl salicylate, glycol salicylate, indomethacin, diclofenac sodium, felbinac, and ketoprofen; skeletal muscle relaxants such as eperisone hydrochloride; antifungal agents such as miconazole and clotrimazole; hormone drugs such as estradiol and testosterone; antihypertensive agents such as clonidine; vasodilators such as nitroglycerin and isosorbide nitrates; smoking cessation adjuvants such as nicotine; bronchodilators such as tulobuterol; antispasmodics such as scopolamine; and analgesics for cancer pain such as fentanyl.

Among the above, it is preferable to use monoterpenes such as menthol, menthol derivatives, camphor, limonene, geraniol, and citronellol; sesquiterpenes such as cedrol; essential oils, such as mint oil and peppermint oil, containing the above substance(s); and salicylic esters such as methyl salicylate and glycol salicylate. These medicaments are particularly effective because they are highly diffusible in the horny layer, which acts as a barrier of transdermal absorption, and thus promote transdermal absorption.

The partition coefficient (1-octanol/water), i.e., log Pow—which indicates a compound's hydrophobicity and hydrophilicity—of the transdermally-absorbable medicament is preferably 0.5 to 13, and more preferably 1.0 to 5. Setting the log Pow within this range improves the releasing properties of the transdermally-absorbable medicament to the skin owing to the generation of heat by the heat generating member 21 and thus allows the medicament's physiological effects to be exerted on the user effectively. When the medicament exhibits such a high lipophilicity, the medicament is released from the water-containing heat generating member 21 even more significantly and sufficiently permeates into the horny layer, which serves as the skin's barrier layer. As a result, the transdermal-absorption promoting effect achieved by heating is improved and thus the medicament's effects can be exerted sufficiently.

The molecular weight of the transdermally-absorbable medicament is preferably 50 to 1000, and more preferably 100 to 500. Setting the molecular weight within this range allows the transdermally-absorbable medicament to be dispersed more evenly within the heat generating composition and improves the releasing properties of the transdermally-absorbable medicament to the skin owing to the generation of heat by the heat generating member 21. Further, the transdermal-absorption promoting effect achieved by heating is improved and the medicament's effects can be exerted sufficiently, thus allowing the medicament's physiological effects to be exerted on the user effectively.

Among the above-described transdermally-absorbable medicaments, medicaments having blood-circulation promoting effects—such as menthol, menthol derivatives, mint oil, peppermint oil, camphor, tocopherol acetate, tocopherol nicotinate, benzyl nicotinate, capsaicin, and capsicum tincture—are suitably used because their effects can further be enhanced in combination with the blood-circulation promoting effect achieved by heating. Nonsteroidal anti-inflammatory agents are also suitably used because they become further more effective in relieving pain in combination with the analgesic effect achieved by heating.

It is particularly preferable to use a cool-feeling agent as the transdermally-absorbable medicament. A cool-feeling agent acts on the wearer's skin to provide a cool-and-refreshing feel to the wearer. Accordingly, when a heat-and-steam generating device 1 containing a cool-feeling agent is used, the user will perceive a cool-and-refreshing feel caused by the cool-feeling agent, but the skin temperature will actually rise due to the heating effect. In this way, both a heating effect (warm stimuli) to the human body and a cool-and-refreshing feel can be provided to the wearer at the same time. Thus, it is possible to effectively suppress the hotness that is likely to be felt when the heat-and-steam generating device 1 is used in hot seasons, especially in the summertime.

Cool-feeling agents that may be used include those used for cosmetic and medicinal purposes, and examples thereof include menthols such as l-menthol and dl-menthol, isopulegol, menthyl acetate, cineol, borneol, thymol, and the like, and derivatives thereof. It is also possible to use, for example, menthyl lactate, 3-1-menthoxypropanediol, N-ethyl-3-p-menthane carboxamide, and essential oils, such as mint oil and peppermint oil, containing menthol. Using these cool-feeling agents can provide a cool-and-refreshing feel to the skin while maintaining the effects achieved by heating, such as blood-circulation promotion, pain relief, and muscle relaxation.

Among the above, particularly using, for example, a menthol such as l-menthol or dl-menthol, a menthol derivative, mint oil, or peppermint oil can dramatically improve the device's usability—even in environments where a user is likely to feel hot, such as during the summertime—because it is possible to provide a cool-and-refreshing feel to the skin while maintaining the effects achieved by heating, such as blood-circulation promotion, pain relief, and muscle relaxation, and thus suppress the hot feel. L-menthol and dl-menthol are used particularly suitably because they not only activate the TRPM8 receptor but also have blood-circulation promoting effects. As mentioned, it is preferable to use such substances that activate the TRPM8 receptor. The TRPM8 receptor exists in the sensory nerve and is activated by cool stimuli of around 25° C. to 28° C. or below. It is also known that, other than by temperature conditions, the TRPM8 receptor is activated by stimuli from chemical substances.

The above-described transdermally-absorbable medicaments may be used singly, or two or more types may be used mixed. From the standpoint of providing suitable physiological effects to the wearer's body, the total amount of transdermally-absorbable medicament(s) contained with respect to the entire mass of the heat generating member 21 is preferably 0.01 to 10% by mass, more preferably 0.1 to 5% by mass, and even more preferably 0.5 to 3% by mass. In cases where two or more types of medicaments are used mixed, it is further effective to use menthol, a menthol derivative, mint oil, or peppermint oil as one of the medicaments because the medicament's transdermal absorption is increased in combination with the transdermal-absorption promoting effect achieved by heating.

Solvent

Regardless of whether the transdermally-absorbable medicament is a solid, a semisolid, or a liquid, mixing of the transdermally-absorbable medicament into the heat generating member 21 can be achieved by adding the medicament together with a solvent to the heat generating member 21. Adding the transdermally-absorbable medicament together with a solvent to the heat generating member 21 allows the transdermally-absorbable medicament to be evenly dispersed throughout the entire heat generating member 21, particularly in cases where the amount of transdermally-absorbable medicament used is small. The solvent can be selected, taking into consideration the compatibility and dissolubility with the transdermally-absorbable medicament. There are also instances where the solvent is preferably an organic solvent that has good compatibility with water, because the heat generating member 21 contains water and generates heat through chemical reaction. Using a solvent having good compatibility with water allows the solvent to be dispersed evenly throughout the heat generating member 21. Such organic solvents may include alcohols that are liquid substances at 25° C., and examples thereof include polyols such as ethylene glycol, propylene glycol, dipropylene glycol, 1,3-butylene glycol, glycerin, polyethylene glycols such as polyethylene glycol 200 and polyethylene glycol 400, polypropylene glycol, and 1,3-propane diet and lower alcohols such as ethanol. Among these, polyols that are liquid substances at 25° C. are particularly preferable because they release a large amount of transdermally-absorbable medicament. Further, among these polyols, polyethylene glycol and dipropylene glycol are particularly preferable from the standpoint of making the transdermally-absorbable medicament's efficacy appear effectively. It is also preferable that the solvent has a weak smell during use, because the present invention involves heat generation through chemical reaction. Among such solvents, polyethylene glycol and propylene glycol are preferred.

The solvent may be used singly, or two or more types may be used mixed. Further, from the standpoint of adding the solvent such that it is dispersed evenly throughout the entire heat generating member 21 and keeping small the solvent's influence on heat generating properties, the solvent is used at a concentration of preferably 0.01 to 20% by mass, more preferably 0.1 to 10% by mass, and even more preferably 0.5 to 5% by mass, with respect to the entire mass of the heat generating member 21. Further, assuming that the total mass of the solvent and the transdermally-absorbable medicament is 100, the solvent is used at a percentage of preferably 5 to 99% by mass, more preferably 10 to 93% by mass, even more preferably 30 to 90% by mass, and further more preferably 50 to 80% by mass.

An embodiment of the present invention for adding the transdermally-absorbable medicament to the heat generating member 21 may include, for example: preparing a solution containing a transdermally-absorbable medicament dissolved in advance into a solvent; and adding the solution to a heat generating member containing an oxidizable metal, a reaction accelerator, an electrolyte, and water. Addition may be achieved through methods such as spraying, coating, or immersion. Specific methods will be described further below along with methods for manufacturing the heat-and-steam generating device 1.

In another embodiment of the present invention, it is preferable to use, particularly as the solvent, a mixture combining two types of solvents (a first solvent and a second solvent) described below. Using the first solvent and second solvent in combination allows the transdermally-absorbable medicament to be released favorably while the heat generating device generates heat.

(A) A first solvent composed of at least one type of oily agent that is in its liquid state at 25° C. and that is selected from a group consisting of hydrocarbon oils, ester oils, monovalent alcohols, fatty acids, silicone oils, and glycerides, and natural vegetable oils at least partially containing one or more of the above;

(B) A second solvent composed of a polyol.

The first solvent is composed of at least one type of oily agent that is in its liquid state at 25° C. and that is selected from a group consisting of hydrocarbon oils, ester oils, monovalent alcohols, fatty acids, silicone oils, and glycerides, and natural vegetable oils at least partially containing one or more of the above. Specific examples thereof include: hydrocarbon oils such as liquid paraffin and squalane; ester oils such as isopropyl myristate, isopropyl palmitate, cetyl 2-ethylhexanoate, octyldodecyl myristate, and neopentyl glycol dicaprate; monovalent alcohols such as 2-hexyldecanol, 2-octyldodecanol, 2-decyltetradecanol, and isostearyl alcohol; fatty acids such as isostearic acid and oleic acid; cyclic or linear silicone oils such as dimethyl polysiloxane, methylphenyl polysiloxane, and cyclomethicone; diglycerides such as dioleic diglyceride; monoglycerides such as diethylhexyl monoglyceride; triglycerides such as glyceryl tricaprylate and caprylic/capric triglyceride; and natural vegetable oils such as jojoba oil, macadamia nut oil, olive oil, and castor oil. Among these, monovalent higher alcohols having a carbon number of 16 to 22 particularly exhibit excellent compatibility with transdermally-absorbable medicaments. Thus, even a small amount of such alcohols can function to evenly blend the transdermally-absorbable medicament into the heat generating composition, and this keeps small the solvent's influence on heat generation. Further, the heat-and-steam generating device 1 is made less prone to smell foul during heat generation.

Containing the first solvent at a percentage of preferably 0.01 to 5% by mass, more preferably 0.05 to 3% by mass, and even more preferably 0.1 to 1% by mass, with respect to the entire mass of the heat generating member 21 is suitable because a sufficient amount of heat generation will be secured. The mass ratio of the first solvent to the transdermally-absorbable medicament (the mass of the first solvent/ the mass of the transdermally-absorbable medicament) is preferably 0.01 to 2, more preferably 0.05 to 1, and even more preferably 0.1 to 0.5.

Examples of polyols used as the second solvent include ethylene glycol, propylene glycol, dipropylene glycol, 1,3-butylene glycol, glycerin, polyethylene glycols such as polyethylene glycol 200 and polyethylene glycol 400, polypropylene glycol, and 1,3-propane diol. Among these, polyethylene glycol is used preferably because it can effectively improve the releasing properties of the transdermally-absorbable medicament. Polyethylene glycol is also preferable in that the emulsifying-and-dispersing properties of the surfactant, which is added as necessary, for emulsifying and dispersing the transdermally-absorbable medicament can be maintained.

Containing the second solvent at a percentage of preferably 0.01 to 5% by mass, more preferably 0.05 to 3% by mass, and even more preferably 0.1 to 2% by mass, with respect to the entire mass of the heat generating member 21 is suitable because a sufficient amount of heat generation will be secured and the properties of releasing the medicament from the heat generating member will be improved. The mass ratio of the second solvent to the transdermally-absorbable medicament (the mass of the second solvent/the mass of the transdermally-absorbable medicament) is preferably 0.1 to 5, more preferably 0.5 to 3, and even more preferably 1 to 2.

Containing the two solvents at the above-mentioned percentages will minimize inhibition of heat generation, thereby resulting in the transdermally-absorbable medicament being released favorably owing to the generation of heat by the heat generating member 21 and the transdermally-absorbable medicament's intrinsic physiological effects being exerted effectively.

The combination of the first and second solvents is selected taking into consideration the solvents' influence on the compatibility between the transdermally-absorbable medicament and water and on the affinity between the later-described surfactant and water. A preferred combination of a first solvent and a second solvent is to use a monovalent higher alcohol as the first solvent and a polyol as the second solvent. Employing this combination will result in the transdermally-absorbable medicament being released favorably upon heat generation by the heat generating member 21 and the transdermally-absorbable medicament's intrinsic physiological effects being exerted even more effectively. Furthermore, employing the above combination will allow the surfactant, which is added as necessary, to emulsify the transdermally-absorbable medicament into the water contained in the heat generating member 21 even more satisfactorily and will minimize inhibition of heat generation. Specific examples of solvents that may be used particularly preferably as the first solvent include 2-octyldodecanol and 2-hexyldecanol. On the other hand, solvents that may be used particularly preferably as the second solvent include polyethylene glycol, particularly polyethylene glycol having a molecular weight of 200 to 600. Note that preferably, the solvents are substances into which the transdermally-absorbable medicament can be dissolved and are organic solvents harmless to the body.

Surfactant

As another embodiment of the present invention, Inventors made diligent research on the emulsifying-and-dispersing properties of the transdermally-absorbable medicament in the heat generating member 21 and the medicament's releasing properties, and found that adding the transdermally-absorbable medicament to the heat generating member along with the specific two types of solvents (the first and second solvents) described above in combination with a surfactant improves the emulsifying-and-dispersing properties of the transdermally-absorbable medicament and also allows the transdermally-absorbable medicament to disperse into the heat generating composition further more evenly. Inventors also found that inhibition of heat generation caused by the transdermally-absorbable medicament and/or the solvents can be minimized and the temperature at which the heat is generated can be maintained favorably. Furthermore, inventors also found that the emulsified state of the transdermally-absorbable medicament is suitably destabilized upon use of the heat generating device, and this allows the transdermally-absorbable medicament to be favorably released.

Any of cationic surfactants, anionic surfactants, nonionic surfactants, and zwitterionic surfactants may be used as the surfactant of the present invention, so long as they can be used in cosmetic and medicinal products. Among these, nonionic surfactants are used advantageously. This is because nonionic surfactants can satisfactorily emulsify the transdermally-absorbable medicament into the aqueous electrolytic solution contained in the heat generating member 21 and achieve high emulsion stability. Further, nonionic surfactants allow the transdermally-absorbable medicament to be released favorably by the generation of heat by the heat generating member 21 and are also less prone to inhibit heat generation of the heat generating member 21.

Examples of nonionic surfactants that may be used include polyoxyethylene alkyl ethers, polyoxyethylene hydrogenated castor oil, polyoxyethylene alkylallyl ethers, sorbitan fatty acid esters, polyoxyethylene sorbitan fatty acid esters, polyoxyethylene sorbitol fatty acid esters, fatty acid monoglycerides, polyoxyethylene fatty acid esters, polyoxyethylene alkylamines, alkylalkanol amides, sucrose fatty acid esters, polyglycerin fatty acid esters, polyoxyethylene fatty acid glycerin, and polyoxyethylene polyoxypropylene copolymers. Among these surfactants, polyoxyethylene-based surfactants are preferable, such as polyoxyethylene alkyl ethers, polyoxyethylene hydrogenated castor oil, polyoxyethylene alkylallyl ethers, polyoxyethylene sorbitan fatty acid esters, polyoxyethylene sorbitol fatty acid esters, polyoxyethylene fatty acid esters, polyoxyethylene alkylamines, polyoxyethylene fatty acid glycerin, and polyoxyethylene polyoxypropylene copolymers. Among these, polyoxyethylene hydrogenated castor oil and polyoxyethylene alkyl ethers are preferable, because they have interaction with the second solvent and also have an effect on the affinity of the surfactant with water. It is particularly advantageous to use polyoxyethylene hydrogenated castor oil or polyoxyethylene alkyl ether—and especially polyoxyethylene hydrogenated castor oil—having an HLB of preferably 10 to 20, more preferably 12 to 18, and even more preferably 13 to 17. The HLB value is calculated from Griffin's formulas (J. Soc. Cosmet. Chem., 1, 311 (1949)).

The content of the surfactant within the heat generating member 21 is preferably 0.01 to 5% by mass, more preferably 0.05 to 3% by mass, and even more preferably 0.1 to 2% by mass, with respect to the entire mass of the heat generating member 21. Setting the content within the above range allows the transdermally-absorbable medicament and the solvent(s) to disperse within the heat generating composition even more favorably and therefore allows the transdermally-absorbable medicament to blend into the heat generating composition further more evenly. Further, the transdermally-absorbable medicament can be released favorably by the generation of heat by the heat generating member 21, while keeping small the influence on heat generation. As particularly regards the relationship with the content of the second solvent, the mass ratio of the second solvent to the surfactant (second solvent/surfactant) is preferably 0.1 to 5, and more preferably 0.5 to 2. Setting the ratio of the second solvent to the surfactant within this range further prevents heat generation by the heat generating member 21 from being inhibited. Furthermore, the emulsion stability between the transdermally-absorbable medicament and the water contained in the heat generating member 21 is further improved, and also the transdermally-absorbable medicament can be released favorably.

Structure

The heat generating member 21 has, for example, the form of a heat generating sheet or heat generating powder. In cases where the heat generating member 21 is a heat generating sheet, the sheet is preferably made by injecting a transdermally-absorbable-medicament-containing electrolytic solution that contains a transdermally-absorbable medicament, a solvent for the transdermally-absorbable medicament, a surfactant used as necessary, an electrolyte, and water into a molded sheet that contains an oxidizable metal, a reaction accelerator, and a fibrous material. Examples of fibrous materials that may be used include: natural fibers such as cotton, kapok, wood pulp, and non-wood pulp; semisynthetic fibers such as rayon, viscose rayon, and cupra rayon; and synthetic high-polymer fibers such as nylon, acrylic fiber, polyethylene, polypropylene, polystyrene, and polyurethane. The average fiber length of the fibrous material is preferably 0.1 to 50 mm, and more preferably 0.2 to 20 mm, from the standpoint of securing the strength of the heat generating sheet and allowing water to disperse in the fibrous material. Examples of heat generating sheets include sheets formed by a wet papermaking technique and laminate structures in which heat generating powder is held in between sheets of paper, etc. The heat generating sheet may be produced by a wet papermaking process disclosed, for example, in US2005/0000827A1 or through extrusion using a die coater. The disclosure of US2005/0000827A1 is incorporated herein by reference.

In cases where the heat generating member 21 is heat generating powder, it is preferably composed of an oxidizable metal, a reaction accelerator, a moisture retaining agent, a transdermally-absorbable medicament, a solvent for the transdermally-absorbable medicament, a surfactant used as necessary, an electrolyte, and water. In cases where the heat-and-steam generating device 1 is intended to be used as a patch, heat generating sheets are preferred to heat generating powders, because steam can be applied evenly whatever posture the wearer takes. Furthermore, heat generating sheets are advantageous over heat generating powders because of the ease of achieving even distribution of exothermic temperature and their great ability to hold oxidizable metals.

The transdemally-absorbable medicament and the solvent tend to slightly inhibit oxidation of the oxidizable metal contained in the heat generating member 21, and this may impair the heat-generating and steam-generating properties of the heat generating member 21. Accordingly, in the present embodiment, it is advantageous to promote oxidation of the oxidizable metal by appropriately adjusting the composition of the heat generating member 21. From this standpoint, in cases where the heat generating member 21 is a heat generating sheet, it is preferable to include 25 to 80 parts by mass of a 1 to 15 percent-by-mass aqueous solution of an electrolyte with respect to 100 parts by mass of a molded sheet that contains 60 to 90% by mass of an oxidizable metal, 5 to 25% by mass of a reaction accelerator, and 5 to 35% by mass of a fibrous material with respect to the total mass of the oxidizable metal, the reaction accelerator, and the fibrous material. On the other hand, in cases where the heat generating member 21 is heat generating powder, it is preferable to include 20 to 70 parts by mass, and more preferably 30 to 60 parts by mass, of a 0.3 to 15 percent-by-mass, and more preferably a 3 to 10 percent-by-mass, aqueous solution of an electrolyte with respect to 100 parts by mass of solids content that contains 20 to 60% by mass and more preferably 25 to 55% by mass of an oxidizable metal, 1.5 to 25% by mass and more preferably 2 to 20% by mass of a reaction accelerator, and 3 to 40% by mass and more preferably 5 to 20% by mass of a moisture-retaining agent with respect to the total mass of the oxidizable metal, the reaction accelerator, and the moisture-retaining agent. The materials constituting the heat generating sheet or heat generating powder can be selected from those commonly used in the art. The materials disclosed in US2005/0000827A1 may be used as well, the disclosure of which is incorporated herein by reference.

Holder

The first side 23 of the holder 22 that constitutes the heat generating element 20 has air permeability to allow for passage of air and steam. The second side 24 is less permeable to air and steam than the first side 23. In other words, the second side 24 is sparingly air-permeable or air-impermeable compared with the first side 23. Whether the second side 24 is sparingly air-permeable or air-impermeable is selected as appropriate for the intended use of the heat-and-steam generating device 1.

The heat generating element 20 is used with its first side 23 facing the wearer's skin and the second side 24 facing the clothing (i.e., outside). Thus, the steam generated by the heat generation of the heat generating member 21 and the components released from the transdermally-absorbable medicament are applied to the wearer's skin, which is the subject of application, through the holder 22 and the bag 10.

Each of the first side 23 and the second side 24 of the heat generating element 20 is formed of a sheet material. The periphery of the sheet material forming the first side 23 and that forming the second side 24 are joined to each other so that the holder 22 of the heat generating element 20 has, in its periphery, a closed loop of a peripheral joint 25. The peripheral joint 25 is continuous. The first side 23 and the second side 24 of the holder 22 are not bonded to each other in the region inside the peripheral joint 25. In this way, the holder 22 provides a single bag-like space in which the heat generating member 21 can be enclosed. As illustrated in FIG. 5(*a*) and FIG. 5(*b*), the heat generating member 21 placed inside the space formed by the holder 22 occupies practically the whole space of the holder 22. To put it another way, the holder 22 contains one heat generating member 21, and the heat generating member 21 occupies practically the whole area of the holder 22 except the peripheral joint 25. In FIG. 5(*a*) and FIG. 5(*b*), the heat generating member 21 is simply placed inside the bag-like space of the holder 22. However, in cases where the heat generating member 21 is a heat generating sheet, the heat generating member 21 and a part of the inner side of the holder 22 may be fixed to each other by joining means, such as an adhesive, in a manner that does not interfere with heat generation.

In the present heat generating element 20, the air permeance of the first side 23 and the air permeance of the second side 24 are suitably adjusted so that steam may be released preferentially through the first side 23. Specifically, the second side is designed to have a higher air permeance than the first side. The term "air permeance" as used herein is a value measured in accordance with JIS P8117, which is defined as the time required for 100 ml of air to pass through an area of 6.45 cm$^2$ under a constant pressure. Therefore, a higher air permeance means more time is needed for air passage, i.e., lower air permeability. Conversely, a lower air permeance means higher air permeability. That is, air permeance and air permeability are in a converse relation. Comparing the air permeability between the first side 23 and the second side 24 in the present embodiment, the first side 23 has higher air permeability than the second side 24. That is, as previously stated, the second side 24 is air impermeable or sparingly air permeable (i.e., air permeable but less air permeable than the first side 23).

The holder 22 has a flat shape having the air-permeable first side 23 and the opposite, air-impermeable second side 24 and is designed to cause steam and heat generation through the air-permeable first side 23. Alternatively, the holder 22 has a flat shape having the air-permeable first side 23 and the opposite, sparingly-air-permeable second side 24 and is designed to cause steam and heat generation through the air-permeable first side 23. In cases where the second side 24 is sparingly air permeable, the air permeance of the first side 23 and that of the second side 24 should be adjusted so that air may enter the holder 22 preferentially through the second side 24 while steam may be released preferentially through the first side 23.

In cases where the second side 24 is sparingly air permeable, it is preferred that the air permeance of the second side 24 is at least 1.5 times, and more preferably at least twice, the air permeance of the first side 23 from the standpoint of suppressing steam release through the second side 24 while securing an air inflow through the same side 24. It is otherwise preferred that the ratio of the air permeance of the first side 23 to that of the second side 24 (first side/second side ratio) is 0.7 or smaller, and more preferably 0.4 or smaller. By so controlling the air permeance, release of steam from the second side 24 can be further reduced while further increasing release of steam from the first side 23. On the other hand, in cases where the second side 24 is air impermeable, entry of air into the holder 22 and release of steam are exclusively done through the first side 23.

As described above, the heat generating member 21 of the heat generating element 20 of the present embodiment contains a transdermally-absorbable medicament and a solvent therefor. The heat generating member 21 also contains a surfactant as necessary. These agents tend to slightly inhibit oxidation of the oxidizable metal contained in the heat generating member 21, thereby giving rise to a tendency of impairing the heat-generating and steam-generating properties of the heat generating member 21. Accordingly, in the present embodiment, it is advantageous to promote oxidation of the oxidizable metal by slightly increasing the air permeance of the first side 23 compared to conventional heat-and-steam generating devices. From this standpoint, the air permeance of the first side 23 is adjusted preferably to 5000 to 25000 sec/100 ml, more preferably 8000 to 22000 sec/100 ml, and even more preferably 10000 to 20000 sec/100 ml. On the other hand, the air permeance of the second side 24, if sparingly air permeable, is adjusted preferably to 30000 sec/100 ml or more, and more preferably 40000 sec/100 ml or more.

Each of the first side 23 and the second side 24 of the heat generating element 20 is formed of a sheet material. Meltblown nonwoven fabrics or moisture permeable films may suitably be used as sheet materials that govern air permeance and prevent powders from escaping. A moisture permeable film is obtainable by melt molding a mixture of a thermoplastic resin and an organic or inorganic filler incompatible with the resin into a film and uniaxially or biaxially stretching the film to develop a finely porous structure. Sheet materials having different air permeances and moisture permeances can be combined to make a laminate sheet. Use of such laminate sheets increases the flexibility in setting the air permeances of the first side 23 and the second side 24 to desired values.

Wrapper

The whole heat-and-steam generating device 1 is packaged in a wrapper (not shown) having oxygen barrier properties so as to protect the heat generating member 21 from coming into contact with oxygen in the air before use. Examples of materials having oxygen barrier properties preferably include those having an oxygen transmission rate (ASTM D3985) of 10 $cm^3 \cdot mm/(m^2 \cdot day \cdot MPa)$ or lower, and more preferably 2 $cm^3 \cdot mm/(m^2 \cdot day \cdot MPa)$ or lower. Specific examples thereof include: films made of ethylene-vinyl alcohol copolymer, polyacrylonitrile, or the like; such films vacuum-deposited with ceramic, aluminum, or the like; and so-called aluminum laminate films.

Manufacturing Method

According to an embodiment of the present invention, the heat-and-steam generating device 1 of the present embodiment is manufactured as follows, for example. First, a heat generating member 21 is prepared by evenly adding, to a mixture containing an oxidizable metal, a reaction accelerator, an electrolyte, and water, a solution obtained by dissolving a transdermally-absorbable medicament into a solvent. A heat generating element 20 can be obtained by placing the heat generating member 21 inside a holder 22. In cases where the heat generating member 21 is a powdery composition, the heat generating element 20 may be manufactured by first mixing the solids contents that constitute the heat generating member 21, such as an oxidizable metal and a reaction accelerator; then adding an aqueous electrolytic solution to the mixture; further adding thereto a solution obtained by dissolving a transdermally-absorbable medicament into a solvent to thus obtain a heat generating member 21; and finally placing the heat generating member 21 inside a holder 22.

On the other hand, in cases where the heat generating member 21 is a molded sheet, the heat generating element 20 may be manufactured by: first preparing a molded sheet containing an oxidizable metal, a reaction accelerator, and a fibrous material; then adding, to the molded sheet, an aqueous electrolytic solution followed by addition of a solution obtained by dissolving a transdermally-absorbable medicament into a solvent, to obtain a heat generating member 21; and finally placing the heat generating member 21 inside a holder 22.

Manufacturing the heat generating element 20 in this way allows the transdermally-absorbable medicament to be dispersed evenly throughout the entire heat generating member 21. The thus-obtained heat generating element 20 is then made into a heat-and-steam generating device 1 by being placed inside a bag 10.

In another embodiment of the present invention, the heat-and-steam generating device 1 may be manufactured as follows, for example. In cases where the heat generating member 21 is a powdery composition, it will suffice if all of the components that constitute the heat generating member 21 are simply mixed together, but a preferred manufacturing method would be as follows. First, the solids contents that constitute the heat generating member 21, such as an oxidizable metal and a reaction accelerator, are mixed together in advance. Meanwhile, a mixture containing a transdermally-absorbable medicament, a solvent, and a surfactant used as necessary is added to an aqueous solution obtained by dissolving an electrolyte into water and the solution is stirred and emulsified (at 300 rpm for 10 minutes), to prepare a transdermally-absorbable-medicament-containing electrolytic solution. Adding and mixing the transdermally-absorbable-medicament-containing electrolytic solution to the solids contents will provide a heat generating member 21, and the heat generating member 21 can be made into a heat generating element 20 by being placed inside a holder 22.

On the other hand, in cases where the heat generating member 21 is a molded sheet, the heat generating element 20 may be manufactured by: first preparing a molded sheet containing an oxidizable metal, a reaction accelerator, and a fibrous material; then injecting, to the molded sheet, a transdermally-absorbable-medicament-containing electrolytic solution prepared in advance in the same way as above, to obtain a heat generating member 21; and finally placing the thus-obtained heat generating member 21 inside a holder 22.

Manufacturing the heat generating element 20 in this way allows the transdermally-absorbable medicament to be dispersed evenly throughout the entire heat generating member 21. The thus-obtained heat generating element 20 is then made into a heat-and-steam generating device 1 by being placed inside a bag 10. Manufacturing the heat-and-steam generating device 1 according to these methods allows the solvent, the transdermally-absorbable medicament, the electrolyte-containing aqueous solution, and the surfactant used as necessary to be added to the heat generating composition all at the same time, thereby resulting in the transdermally-absorbable medicament being evenly dispersed throughout the entire heat generating composition and in further stabilization of heat generation. Particularly, in cases where the heat generating member 21 consists of a molded sheet, the penetrability of the surfactant used as necessary, the solvent, the transdermally-absorbable medicament, and the electrolyte-containing aqueous solution into the molded sheet is dramatically improved, which in turn improves the even dispersion of the transdermally-absorbable medicament within the heat generating composition and also allows further stabilization of heat generation.

Other Embodiments

The present invention has been described above according to preferred embodiments thereof, but the invention is not to be limited to those embodiments. For example, the foregoing embodiments relate to application of the heat generating device of the present invention to a heat-and-steam generating device, but the invention is also applicable to other heat generating implements other than heat-and-steam generating devices, including those known as disposable body warmers or heating pads that release only an extremely small amount of steam. In such applications, heating will accelerate skin blood flow, which in turn improves the transferability of the medicament to subcutaneous tissues, thereby achieving transdermal-absorption promoting effects. Nevertheless, the heat generating device of the foregoing embodiment that generates both heat and steam allows the transdermally-absorbable medicament to achieve a higher degree of physiological effectiveness on the wearer. This is because the steam causes swelling of the skin's horny layer, which acts as a barrier layer, and allows the medicament to penetrate easier into the skin. For example, in cases where a cool-feeling agent is used as the transdermally-absorbable medicament, the heat generating device of the foregoing embodiment that generates both heat and steam provides a stronger cool-and-refreshing feel by the action of the cool-feeling agent.

The foregoing embodiment mentioned that the heat generating element 20 may be placed in a bag 10 having stretchability, but a bag that is not stretchable may be used instead.

The heat-and-steam generating device 1 of the foregoing embodiment is designed to be stuck on the wearer's body, but instead, the heat-and-steam generating device 1 may be used as a mask or eye mask, by being stuck on the wearer's clothing, or by being placed on the body with the hand. In cases of sticking the heat-and-steam generating device 1 on the clothing, attachment means such as an adhesive may be provided on the surface of the second sheet 12 of the bag 10.

EXAMPLES

The present invention will now be described in greater detail by way of Examples, but the scope of the invention shall not be limited thereto. Unless otherwise noted, "%" and "parts" mean "% by mass" and "parts by mass".

Example 1

A heat-and-steam generating device 1 according to the embodiment illustrated in FIGS. 1 to 6 was made in accordance with the following procedures.

(1) Preparation of Sheet-Shaped Heat Generating Member 21

Content of Raw Material Composition of Molded Sheet:
Oxidizable Metal: 83%
  Iron powder ("RICH" (trade name) available from Dowa Mining Co., Ltd.)
Fibrous Material: 8%
  Pulp fiber (NBKP "Mackenzi" (trade name) available from Fletcher Challenge Canada Ltd.; CSF: adjusted to 200 ml)
Reaction Accelerator: 9%
  Activated carbon ("Carboraffin" (trade name) available from Japan EnviroChemicals, Ltd.; average particle diameter: 45 μm)

To 100 parts of the solids contents of the raw material composition (i.e., mixture of the oxidizable metal, the fibrous material, and the activated carbon) were added 0.7 parts of a polyamide-epichlorohydrin resin ("WS4020" (trade name) available from Seiko PMC Corp.) as a cationic flocculant and 0.18 parts of sodium carboxymethyl cellulose ("HE1500F" (trade name) available from Dai-ichi Kogyo Seiyaku Co., Ltd.) as an anionic flocculant. Water (industrial water) was added to the mixture to prepare a slurry having a solids concentration of 12%.

Papermaking Conditions

The thus-prepared slurry was diluted with water to 0.3% in front of the papermaking head box and drained on an inclined short-wire paper machine at a line speed of 15 m/min to form a wet molded sheet.

Drying Conditions

The molded sheet was pressurized and dewatered between felt blankets, passed as such between 140° C. heated rollers to be dried to a water content of 5% or less. The dried sheet had a basis weight of 450 g/m² and a thickness of 0.45 mm. As a result of measurement with a thermogravimetric analyzer (TG/DTA 6200 available from Seiko Instruments Inc.), the resultant molded sheet was found to be made up of 83% iron, 9% activated carbon, and 8% pulp.

Injection of Transdermally-Absorbable-Medicament-Containing Electrolytic Solution into Molded Sheet The thus-molded sheet was cut so as to obtain pieces each being 49 mm wide and 49 mm long, and three of these pieces were placed one upon another. To 100 parts of this molded-sheet laminate was injected 45 parts of a menthol-containing electrolytic solution prepared to have the composition shown in Table 1 below. The solution was allowed to penetrate throughout the entire molded sheet utilizing capillarity, to obtain a square sheet-shaped heat generating member 21, wherein 0.9% of menthol, 0.2% of 2-octyldodecanol, 1.4% of polyethylene glycol, and 0.9% of polyoxyethylene hydrogenated castor oil (60 E.O.) (HLB: 14.0) were contained with respect to the entire mass of the heat generating member 21.

TABLE 1

|  | content (% by mass) |
| --- | --- |
| l-menthol | 3.0% |
| polyethylene glycol 400 | 4.4% |
| 2-octyldodecanol | 0.7% |
| polyoxyethylene hydrogenated castor oil | 3.0% |
| sodium chloride | 8.0% |
| purified water | remainder |
| total | 100.0% |

(2) Preparation of Heat Generating Element 20

A heat generating element 20 was obtained using the films mentioned below for the first side 23 and the second side 24 of the holder 22. The heat generating element 20 was placed inside a bag 10 made of stretch sheets 11, 12 mentioned below. A hot-melt adhesive made of SIS copolymer was used for attachment of the sheets 11, 12 and the heat generating element 20. Further, attachment means 2 was provided on the surface of the first stretch sheet 11 using a hot-melt adhesive made of SIS copolymer, to thus obtain a heat-and-steam generating device 1.

The first side 23 of the holder 22 was made of a polyethylene moisture-permeable film having an air permeance of 15000 sec/100 ml. The second side 24 was made of a polyethylene moisture-permeable film having an air permeance of 60000 sec/100 ml. The stretch sheet 11 of the bag 10 was made of a polyethylene terephthalate nonwoven having a basis weight of 38 g/m², and the stretch sheet 12 was made of a polypropylene nonwoven having a basis weight of 50 g/m².

Comparative Example 1

A heat-and-steam generating device was prepared in the same way as in Example 1, except that a menthol-containing electrolytic solution prepared to have the composition shown in Table 2 below was used.

TABLE 2

|  | content (% by mass) |
| --- | --- |
| l-menthol | 3.0% |
| 2-octyldodecanol | 0.7% |
| polyoxyethylene hydrogenated castor oil | 3.0% |
| sodium chloride | 8.0% |
| purified water | remainder |
| total | 100.0% |

Evaluation 1

The quantity of menthol released upon heat generation from the respective sheets of the heat-and-steam generating devices prepared according to Example 1 and Comparative Example 1 was determined using a medicament release amount measurement apparatus described below. The results are shown in Table 3. From the heat-and-steam generating device of Example 1 containing polyethylene glycol as the second solvent, 1.9 mg of menthol was collected in 2 hours, whereas from the heat-and-steam generating device of Comparative Example 1 was collected 1.0 mg of menthol. The results provided in Table 3 clearly show that the heat-and-steam generating device of the present invention exhibits superior menthol-releasing properties.

TABLE 3

| Amount of Menthol Released (mg/2 hr) | |
|---|---|
| Example 1 | Comparative Example 1 |
| 1.9 | 1.0 |

Medicament Release Amount Measurement Apparatus

Figure 7:
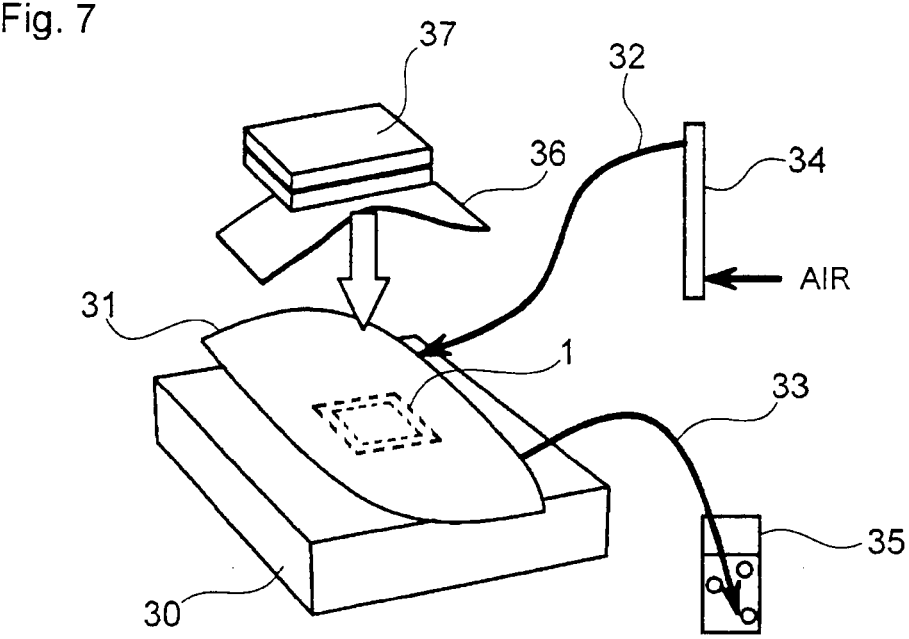
FIG. 7 is a conceptual diagram of a medicament release amount measurement apparatus.

As illustrated in FIG. 7, either the heat-and-steam generating device 1 of Example 1 or that of Comparative Example 1 was enclosed in a bag 31 made of vinyl fluoride resin (such as a Tedlar bag), and the bag 31 was placed on a hot plate 30 heated to 35° C. One end of a tube 32 and one end of a tube 33 were connected to the vinyl fluoride bag 31. The other end of the tube 32 was connected to an air supply source (not shown) via a flowmeter 34. The other end of the tube 33 was immersed in ethanol contained in a container 35. The vinyl fluoride bag 31 was entirely covered with a polypropylene nonwoven fabric 36 for heat insulation. Further, a weight 37 was placed on the nonwoven fabric 36 so that the heat-and-steam generating device 1 does not move out of place when air is supplied into the vinyl fluoride bag 31. While air was being supplied into the vinyl fluoride bag 31 (at 100 ml/minutes) from the air supply source (not shown) through the tube 32, the gas released upon heat generation was ejected into the ethanol through the tube 33, thereby collecting menthol in the ethanol. The quantity of methanol collected after two hours was determined through gas chromatography (using "6890N Network GC system" available from Agilent Technologies, Inc.). Note that the heat-and-steam generating device 1 enclosed inside the vinyl fluoride bag 31 was one of the two connected heat-and-steam generating devices 1 illustrated in FIG. 1 separated from the other.

Evaluation 2

The heat-and-steam generating devices prepared according to Example 1 and Comparative Example 1 were used to conduct a patch test on the right and left shoulders of 10 test subjects. The heat-and-steam generating device of Example 1 was attached to either the left or right shoulder of each test subject, and the heat-and-steam generating device of Comparative Example 1 was attached to the other shoulder. After leaving the devices on the shoulders for 6 hours, evaluation was made on how fast a cool-and-refreshing feel was felt and how strong the cool-and-refreshing feel was. The results are shown in Table 4. The results provided in Table 4 clearly show that the heat-and-steam generating device of Example 1 exhibited a significantly favorable cool-and-refreshing feel caused by menthol, because of its superior menthol-releasing properties.

TABLE 4

| | Example 1 | Comparative Example 1 |
|---|---|---|
| Device providing cool-and-refreshing feel faster | 9 people | 1 person |
| Device providing stronger cool-and-refreshing feel | 10 people | none |

Examples 2 to 11

Heat-and-steam generating devices were prepared in the same way as in Example 1, except that the contents of the components constituting each heat generating member were set to those shown in Table 5 below. The prepared heat-and-steam generating devices were attached to the shoulders of 5 test subjects. The cool-and-refreshing feel and the smell (foul smell other than menthol scent) while each heat-and-steam generating device was attached, as well as an overall evaluation, were evaluated by the test subjects according to the following criteria. Table 5 shows evaluation results taken from the majority of the test subjects. Note that Table 5 also shows the evaluation results for Example 1 and Comparative Example 1.

Cool-and-Refreshing Feel:
6: Very strong and favorable cool-and-refreshing feel
5: Very favorable cool-and-refreshing feel
4: Moderate cool-and-refreshing feel
3: Somewhat weak cool-and-refreshing feel
2: Very weak cool-and-refreshing feel
1: No cool-and-refreshing feel Smell:
A: No foul smell
B: Weak foul smell
F: Strong foul smell Overall Evaluation:
A: Very comfortable in hot environment
B: Comfortable in hot environment
D: Not so comfortable in hot environment
F: Not comfortable in hot environment at all

TABLE 5

| | | | Values indicate content (% by mass) | | | | | |
|---|---|---|---|---|---|---|---|---|
| | | | Examples | | | | | |
| | | | 1 | 2 | 3 | 4 | 5 | 6 |
| heat generating member | molded sheet | iron powder/pulp fiber/activated carbon (=83/8/9) | 69.0 | 69.0 | 69.0 | 69.0 | 69.0 | 69.0 |
| | transdermally-absorbable medicament | l-menthol | 0.9 | 0.9 | 0.9 | 0.9 | 0.9 | |
| | | dl-menthol | | | | | | 0.9 |
| | | menthyl lactate | | | | | | |
| | | methyl salicylate | | | | | | |

TABLE 5-continued

| | | | \multicolumn{6}{c}{Values indicate content (% by mass)} |
|---|---|---|---|---|---|---|---|---|
| first solvent | 2-octyldodecanol | 0.2 | 0.2 | 0.2 | | 0.2 | 0.2 |
| | isopropyl palmitate | | | | 0.2 | | |
| second solvent | polyethylene glycol 400 | 1.4 | | | | 1.4 | 1.4 |
| | propylene glycol | | 1.4 | | | | |
| | dipropylene glycol | | | 1.4 | | | |
| surfactant | polyoxyethylene hydrogenated castor oil | 0.9 | 0.9 | 0.9 | 0.9 | | 0.9 |
| | polyoxyethylene alkyl ether | | | | | 0.9 | |
| electrolytic solution | sodium chloride | 2.5 | 2.5 | 2.5 | 2.5 | 2.5 | 2.5 |
| | purified water | 25.1 | 25.1 | 25.1 | 25.1 | 25.1 | 25.1 |
| total | | 100.00 | 100.00 | 100.00 | 100.00 | 100.00 | 100.00 |
| first solvent/transdermally-absorbable medicament | | 0.22 | 0.22 | 0.22 | 0.22 | 0.22 | 0.22 |
| second solvent/transdermally-absorbable medicament | | 1.56 | 1.56 | 1.56 | 1.56 | 1.56 | 1.56 |
| evaluation | cool-and-refreshing feel | 5 | 4 | 5 | 5 | 5 | 4 |
| | smell | A | A | B | B | A | A |
| | overall evaluation | A | B | B | B | A | B |

| | | | \multicolumn{5}{c|}{Examples} | Comp. |
|---|---|---|---|---|---|---|---|---|
| | | | 7 | 8 | 9 | 10 | 11 | Ex. 1 |
| heat generating member | molded sheet | iron powder/pulp fiber/activated carbon (=83/8/9) | 69.8 | 66.7 | 69.3 | 68.2 | 67.3 | 69.9 |
| | transdermally-absorbable medicament | l-menthol | 1.0 | 0.9 | 1.0 | 0.9 | 0.9 | 0.9 |
| | | dl-menthol | | | | | | |
| | | menthyl lactate | | | | | 2.5 | |
| | | methyl salicylate | | | | | | |
| | first solvent | 2-octyldodecanol | 0.2 | 0.2 | 0.01 | 1.8 | 0.2 | 0.2 |
| | | isopropyl palmitate | | | | | | |
| | second solvent | polyethylene glycol 400 | 0.1 | 4.5 | 1.0 | 0.9 | 1.3 | |
| | | propylene glycol | | | | | | |
| | | dipropylene glycol | | | | | | |
| | surfactant | polyoxyethylene hydrogenated castor oil | 1.0 | 0.9 | 1.0 | 0.9 | 0.9 | 0.9 |
| | | polyoxyethylene alkyl ether | | | | | | |
| | electrolytic solution | sodium chloride | 2.5 | 2.5 | 2.5 | 2.5 | 2.4 | 2.5 |
| | | purified water | 25.4 | 24.3 | 25.19 | 24.8 | 24.5 | 25.6 |
| total | | | 100.00 | 100.00 | 100.00 | 100.00 | 100.00 | 100.00 |
| first solvent/transdermally-absorbable medicament | | | 0.20 | 0.22 | 0.01 | 2.00 | 0.06 | 0.22 |
| second solvent/transdermally-absorbable medicament | | | 0.10 | 5.00 | 1.00 | 1.00 | 0.38 | 0.00 |
| evaluation | cool-and-refreshing feel | | 3 | 3 | 4 | 3 | 6 | 2 |
| | smell | | A | B | A | A | A | A |
| | overall evaluation | | B | B | B | B | A | D |

The results provided in Table 5 clearly show that the heat-and-steam generating devices of the present Examples can provide a cool-and-refreshing feel to the user while preventing foul smell from arising. In contrast, the heat-and-steam generating device of Comparative Example 1 was found to have an extremely small effect of providing a cool-and-refreshing feel to the user, although it did not give off a foul smell.

Example 12 and Comparative Examples 2 and 3

To 100 parts of a molded sheet prepared in the same way as the molded sheet of Example 1 was injected 45 parts of an electrolytic solution (5% saline solution). Further, to 100 parts of the molded sheet was injected 6.8 parts of a menthol solution (the menthol solution containing 20 parts of l-menthol and 80 parts of polyethylene glycol 400). These solutions were allowed to penetrate throughout the entire molded sheet utilizing capillarity, to obtain a square sheet-shaped heat generating member 21, wherein the concentration of menthol was 0.90% and the concentration of polyethylene glycol 400 was 3.6% with respect to the entire mass of the heat generating member 21. On the other hand, in Comparative Example 2, no menthol solution was injected. Further, in Comparative Example 3, only the same amount of l-menthol as in Example 12 was added to the heat generating member, without adding any solvent (polyethylene glycol 400). Apart from these points, heat-and-steam generating devices 1 were prepared in the same way as in Example 1. The compositions of the heat-and-steam generating devices 1 are shown in Table 6.

TABLE 6

|  |  | Example 12 | Comparative Example 2 | Comparative Example 3 |
|---|---|---|---|---|
| heat generating member 20 | amount of electrolytic solution (to 100 parts of molded sheet) | 45 parts | 45 parts | 45 parts |
|  | menthol addition (to 100 parts of molded sheet) | 6.8 parts (as menthol solution containing 20 parts l-menthol and 80 parts polyethylene glycol 400) | none | 1.4 parts (only l-menthol) |
|  | first side 23 | polyethylene moisture-permeable film air permeance: 15000 sec/100 ml | polyethylene moisture-permeable film air permeance: 20000 sec/100 ml | polyethylene moisture-permeable film air permeance: 15000 sec/100 ml |
|  | second side 24 | polyethylene moisture-permeable film air permeance: 50000 sec/100 ml | polyethylene moisture-permeable film air permeance: 80000 sec/100 ml | polyethylene moisture-permeable film air permeance: 50000 sec/100 ml |
| bag 10 | stretch sheet 11 | polyethylene terephthalate nonwoven basis weight: 38 g/m$^2$ | polyethylene terephthalate nonwoven basis weight: 38 g/m$^2$ | polyethylene terephthalate nonwoven basis weight: 38 g/m$^2$ |
|  | stretch sheet 12 | polypropylene nonwoven basis weight: 50 g/m$^2$ | polypropylene nonwoven basis weight: 50 g/m$^2$ | polypropylene nonwoven basis weight: 50 g/m$^2$ |

Evaluation 1 described above was made for the heat-and-steam generating devices prepared according to Example 12 and Comparative Example 3. Evaluations 3 and 4 described below were also made.

Evaluation 1

The quantity of menthol released upon heat generation from the respective sheets was determined. The results thereof provided in Table 7 show that 1.7 mg of menthol was collected in 2 hours from the heat-and-steam generating device of Example 12 containing a solvent (polyethylene glycol 400), whereas only 0.15 mg of menthol was collected from the heat-and-steam generating device of Comparative Example 3 containing no solvent. The results provided in Table 7 show that the heat-and-steam generating device of the present invention exhibits superior menthol-releasing properties.

TABLE 7

| Amount of Menthol Released (mg/2 hr) | |
|---|---|
| Example 12 | Comparative Example 3 |
| 1.7 | 0.15 |

Evaluation 3

Heat generating devices prepared according to Example 12 were attached to the shoulders of one female test subject and the autonomic nervous activity was monitored using a polygraph ("Task Force Monitor 3040i" available from Nihon Kohden Corporation) in a hot environment (room temperature: 31.5° C.). In a separate test, heat-and-steam generating devices prepared according to Comparative Example 2 were attached to the shoulders of the same test subject and the autonomic nervous activity was monitored likewise. The results were that the heat-and-steam generating devices of Comparative Example 2 not containing l-menthol increased the sympathetic nervous activity, whereas the heat-and-steam generating device of Example 12 containing l-menthol suppressed the sympathetic nervous activity, making the parasympathetic nervous activity dominant. The test subject also subjectively stated that her whole body felt very hot during the test when she wore the heat-and-steam generating device of Comparative Example 2, but the heat-and-steam generating device of Example 12 felt less hot and was comfortable.

Evaluation 4

Figure 8:
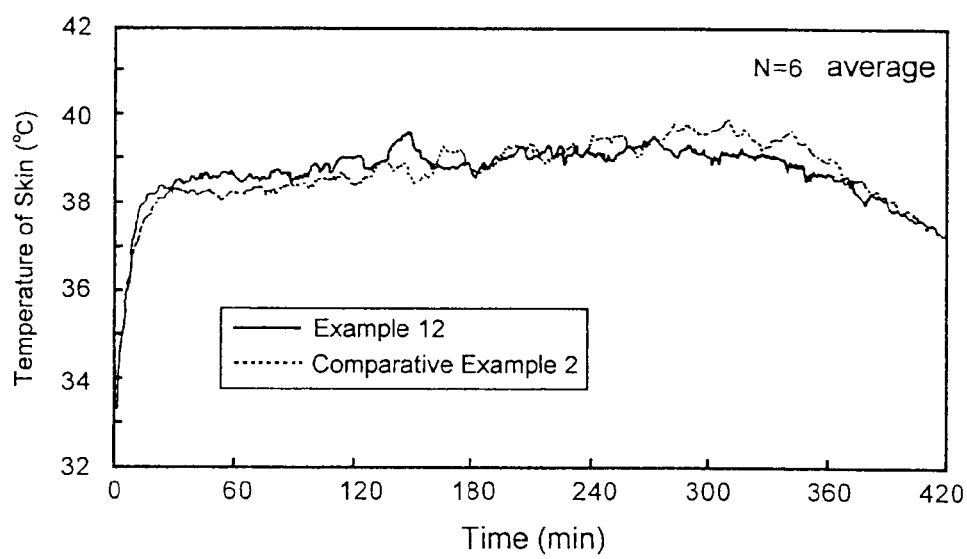
FIG. 8 is a graph illustrating the change over time in skin temperature for when heat generating devices prepared according to Example 12 and Comparative Example 2 were attached to test subjects.

Heat-and-steam generating devices prepared according to Example 12 and Comparative Example 2 were attached respectively to the left and right shoulders of 10 male test subjects for 6 hours in a 25° C. environment, and the sensation perceived during that time was evaluated. Both the heat-and-steam generating devices of Example 12 and Comparative Example 2 exhibited substantially the same skin temperature of around 40° C. while worn (as shown in FIG. 8). The results of the sensation evaluation were that 5 out of the 10 test subjects stated that the heat-and-steam generating device of Example 12 "felt cool rather than hot", whereas none of the test subjects stated that the heat-and-steam generating device of Comparative Example 2 "felt cool rather than hot". Further, 9 out of the 10 test subjects stated that the heat-and-steam generating device of Example 12 "can be used comfortably even in the summertime", whereas 7 out of the 10 test subjects stated that the heat-and-steam generating device of Comparative Example 2 "cannot be used comfortably in the summertime". Note that the temperature graph of FIG. 8 was obtained by measuring the skin temperature at the center of the area where the heat generating member was applied using a handy-type data-logging thermometer "LT-8" available from Gram Corporation.

Examples 13 to 20

Heat-and-steam generating devices were prepared in the same way as in Example 12, except that the types and amounts of the transdermally-absorbable medicament and the solvent were changed to those shown in Table 8 below. The prepared heat-and-steam generating devices were attached to the shoulders of 5 test subjects. The cool-and-refreshing feel and the smell (foul smell other than menthol scent) while each heat-and-steam generating device was attached, as well as an overall evaluation, were evaluated by the test subjects according to the criteria described above. Table 8 shows evaluation results taken from the majority of the test subjects. Note that Table 8 also shows the evaluation results for Example 12 and Comparative Examples 2 and 3.

TABLE 8

| | | | Examples | | | | | | | | | Comparative Examples | |
|---|---|---|---|---|---|---|---|---|---|---|---|---|---|
| | | | 12 | 13 | 14 | 15 | 16 | 17 | 18 | 19 | 20 | 2 | 3 |
| heat generating member | | molded sheet (%) | 65.9 | 65.9 | 65.9 | 65.9 | 65.9 | 60.6 | 67.7 | 70.7 | 63.7 | 69.0 | 68.3 |
| | cool-feeling agent (%) | l-menthol | 0.9 | 0.9 | 0.9 | 0.9 | | | 0.9 | 0.9 | 0.8 | | 0.9 |
| | | dl-menthol | | | | | 0.9 | | | | | | |
| | | menthyl lactate | | | | | | 2.4 | | | | | |
| | solvent (%) | polyethylene glycol 400 | 3.6 | | | | 3.6 | 9.7 | | | 0.1 | 10 | |
| | | propylene glycol | | 3.6 | | | | | | | | | |
| | | dipropylene glycol | | | 3.6 | | | | | | | | |
| | | glycerin | | | | 3.6 | | | | | | | |
| | | ethanol | | | | | | | | 0.9 | | | |
| | electrolytic solution (%) | 5% saline solution | 29.6 | 29.6 | 29.6 | 29.6 | 29.6 | 27.3 | 30.5 | 28.3 | 25.5 | 31.0 | 30.8 |
| | total (%) | | 100.0 | 100.0 | 100.0 | 100.0 | 100.0 | 100.0 | 100.0 | 100.0 | 100.0 | 100.0 | 100.0 |
| | evaluation | cool-and-refreshing feel | 5 | 3 | 4 | 3 | 4 | 3 | 3 | 3 | 4 | 1 | 2 |
| | | smell | A | A | B | B | A | A | A | A | B | A | A |
| | | overall evaluation | A | B | B | B | B | B | B | B | B | F | D |

The results provided in Table 8 clearly show that the heat-and-steam generating devices of the present Examples can provide a cool-and-refreshing feel to the user while preventing foul smell from arising. In contrast, the heat-and-steam generating devices of the Comparative Examples were found to provide hardly any cool-and-refreshing feel to the user, although they did not give of a foul smell.

The invention claimed is:

1. A heat generating device, comprising a holder and a heat generating member that is enclosed in said holder, wherein said heat generating member comprises an oxidizable metal, a reaction accelerator, an electrolyte, water, a transdermally-absorbable medicament and a polyol operable for dissolving said transdermally-absorbable medicament,
    wherein said polyol is in the liquid state at 25° C. and an amount of the polyol is from 0.01 to 5% by mass based on the total mass of the heat generating member, and
    wherein a mass ratio of the polyol that is in the liquid state at 25° C. to the transdermally-absorbable medicament is from 0.1 to 5.

2. The heat generating device according to claim 1, wherein the polyol is polyethylene glycol.

3. The heat generating device according to claim 1, wherein the heat generating member further comprises a surfactant.

4. The heat generating device according to claim 3, wherein the surfactant is a nonionic surfactant.

5. The heat generating device according to claim 1, wherein the transdermally-absorbable medicament is a cool-feeling agent that provides a cool feeling to the skin.

6. The heat generating device according to claim 5, wherein a concentration of the cool-feeling agent in the heat generating member is 0.01 to 10% by mass with respect to the entire mass of the heat generating member.

7. The heat generating device according to claim 5, wherein the cool-feeling agent is at least one member selected from the group consisting of l-menthol, dl-menthol, a derivative of l-menthol or dl-menthol, mint oil, and peppermint oil.

8. The heat generating device according to claim 1, wherein the heat generating member is a sheet comprising the oxidizable metal, the reaction accelerator, the electrolyte, a fibrous material, and the water.

9. A method of manufacturing the heat generating device according to claim 1, the method comprising:
    dissolving a transdermally-absorbable medicament into a polyol to obtain a solution, and
    adding a mixture comprising an oxidizable metal, a reaction accelerator, an electrolyte and water to said solution, to obtain a heat generating member,
    wherein said polyol is in the liquid state at 25° C. and an amount of polyol is from 0.01 to 5% by mass based on the total mass of said heat generating member, and
    wherein a mass ratio of the polyol that is in the liquid state at 25° C. to the mass of the transdermally-absorbable medicament is from 0.1 to 5.

* * * * *